United States Patent [19]

Forfitt et al.

[11] Patent Number: 6,032,100
[45] Date of Patent: Feb. 29, 2000

[54] METHOD AND APPARATUS FOR MONITORING A LUBRICANT

[75] Inventors: Roy Forfitt, White Parish; Honor Powrie, Southampton, both of United Kingdom

[73] Assignee: Stewart Hughes Limited, Eastleigh, United Kingdom

[21] Appl. No.: 08/973,659

[22] PCT Filed: Jun. 12, 1996

[86] PCT No.: PCT/GB96/01407

§ 371 Date: Mar. 25, 1998

§ 102(e) Date: Mar. 25, 1998

[87] PCT Pub. No.: WO97/01093

PCT Pub. Date: Jan. 9, 1997

[30] Foreign Application Priority Data

Jun. 22, 1995 [GB] United Kingdom .................... 9513202

[51] Int. Cl.[7] .................................................. G01N 27/60
[52] U.S. Cl. ...................................................... 702/1; 702/6
[58] Field of Search ............................... 702/5, 10, 1, 6; 324/454, 453, 452; 367/33

[56] References Cited

U.S. PATENT DOCUMENTS

| | | | |
|---|---|---|---|
| 4,629,334 | 12/1986 | Hochstein | 374/103 |
| 4,651,091 | 3/1987 | Chambers et al. | 324/204 |
| 4,766,373 | 8/1988 | Chambers et al. | 324/204 |
| 4,841,244 | 6/1989 | Chambers | 324/204 |
| 5,382,942 | 1/1995 | Raffa et al. | 340/457.4 |
| 5,448,172 | 9/1995 | Dechene et al. | 324/454 |
| 5,559,494 | 9/1996 | Thompson | 340/449 |
| 5,760,298 | 6/1998 | Fisher et al. | 73/61.42 |

FOREIGN PATENT DOCUMENTS

92/09886  6/1992  WIPO .................. 73/61.42

*Primary Examiner*—Christine K. Oda
*Assistant Examiner*—Victor J. Taylor
*Attorney, Agent, or Firm*—Robert E. Ardis; Irwin Ostroff

[57] ABSTRACT

An apparatus for monitoring a lubricant in a machine comprises sensors S1, S2 for producing signals representing electrostatic activity in a machine lubricant and a temperature sensor for producing a signal representative of the temperature of the lubricant. A signal processor 9 is arranged to process the signals from the sensors S1, S2 to detect an electrostatic activity precursor indicative of an impending wear event in the machine. The signal processor is arranged to operate in response to the temperature sensor to compensate for temperature related changes to the signals from the electrostatic sensors S1, S2.

20 Claims, 2 Drawing Sheets

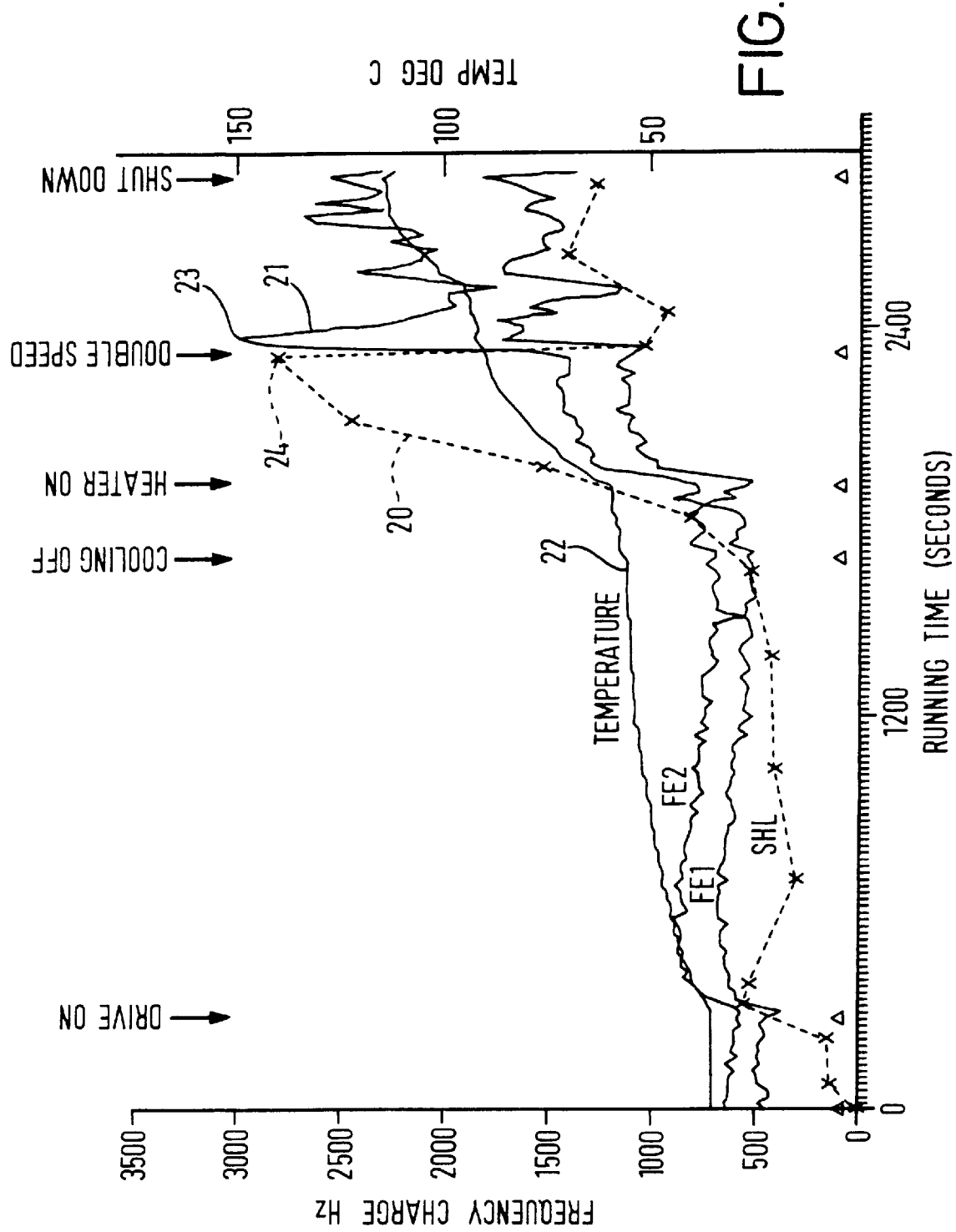

METHOD AND APPARATUS FOR MONITORING A LUBRICANT

FIELD OF THE INVENTION

The invention relates to an apparatus for and method of monitoring lubrication. The invention can be applied to the monitoring of lubrication in a machine for example to enable advance detection of wear in the machine. As used herein the term "machine" is intended to include engines, gearboxes and other mechanical systems in which fluid lubrication is used.

BACKGROUND OF THE INVENTION

In International Patent Application No. PCT/GB 91/02112 published as WO 92/09886 there is described a system for monitoring debris in a fluid. The system comprises at least one electrostatic sensor for producing a signal representing electrostatic charge associated with the fluid moving past the sensor and with debris and/or impurities carried by the fluid. The signal from the sensor is conditioned by a signal conditioner and the conditioned signal is processed by a signal processor together with another signal representing at least the charge associated with the moving fluid in order to produce a signal representing the electrostatic charge associated with the debris and/or impurities. In practice two electrostatic sensors are used at spaced apart locations and the signals therefrom are processed, i.e. correlated, in order to identify the existence of debris in the moving fluid. The system is extremely useful for detecting wear in machines because machine wear causes charge carrying particles to be generated which can be detected by the system.

SUMMARY OF THE INVENTION

In one aspect the invention provides an apparatus for monitoring a lubricant in a machine, the apparatus comprising a sensor for producing a signal representing electrostatic activity in a machine lubricant, and a signal processor for processing the signal from the sensor to detect an electrostatic activity precursor indicative of an impending wear event in the machine.

In another aspect the invention provides a method of monitoring a lubricant in a machine, the method comprising producing a signal representing electrostatic activity in a machine lubricant, and processing the signal to detect an electrostatic activity precursor indicative of an impending wear event in the machine.

In another aspect the invention provides a method of and system for anticipating wear in a machine by monitoring the lubricant thereof for an electrostatic activity precursor indicative of an impending wear event.

In another aspect the invention provides a method of and system for monitoring a machine lubricating fluid, in which method and system the activity level of an electrostatic signal is monitored for a change which is interpreted as a precursor to an electrostatic event corresponding to a wear event.

The detection of a precursor may be utilised to activate an indicator in advance of the wear/electrostatic even to enable corrective action to be taken to avoid the event. Thus, wear or even catastrophic failure in a machine may be avoided as a result of the advance warning enabled by the invention.

BRIEF DESCRIPTION OF THE DRAWINGS

An exemplary embodiment of the invention will be described hereinafter with reference to the accompanying drawings in which:

FIG. 2 shows signals derived from various sensors in the system of FIG. 1.

Turning now to FIG. 1 of the accompanying drawings there is shown a gearbox 1 with an associated oil pump 2 connected to the gearbox 1 by way of a conduit 3. The conduit 3 provides a path for oil from the gearbox to the pump 2 and from the pump to the gearbox. Two sensors S1 and S2 are mounted to the conduit 3 some distance apart from each other. The sensors S1, S2 are provided for sensing electrostatic charge and any suitable form of sensor may be used. Electrical cables 5, 6 from the sensors S1, S2 are connected to a signal conditioner 7. The signal conditioner 7 is provided to perform a preliminary conditioning of the signals from the sensors S1, S2. The signals from the sensors S1, S2 are induced by electrostatic charge passing the sensors. As such the signals tend to be weak, one purpose of the signal conditioner 7 is to give robustness to the signals. The signal conditioner 7 may also act as a coarse filter to remove noise from the signals and may even include integrating and differentiating circuits if so required. Signal conditioning and signal conditioning circuits are per se well known and will not be described in any greater detail herein.

Figure 1:
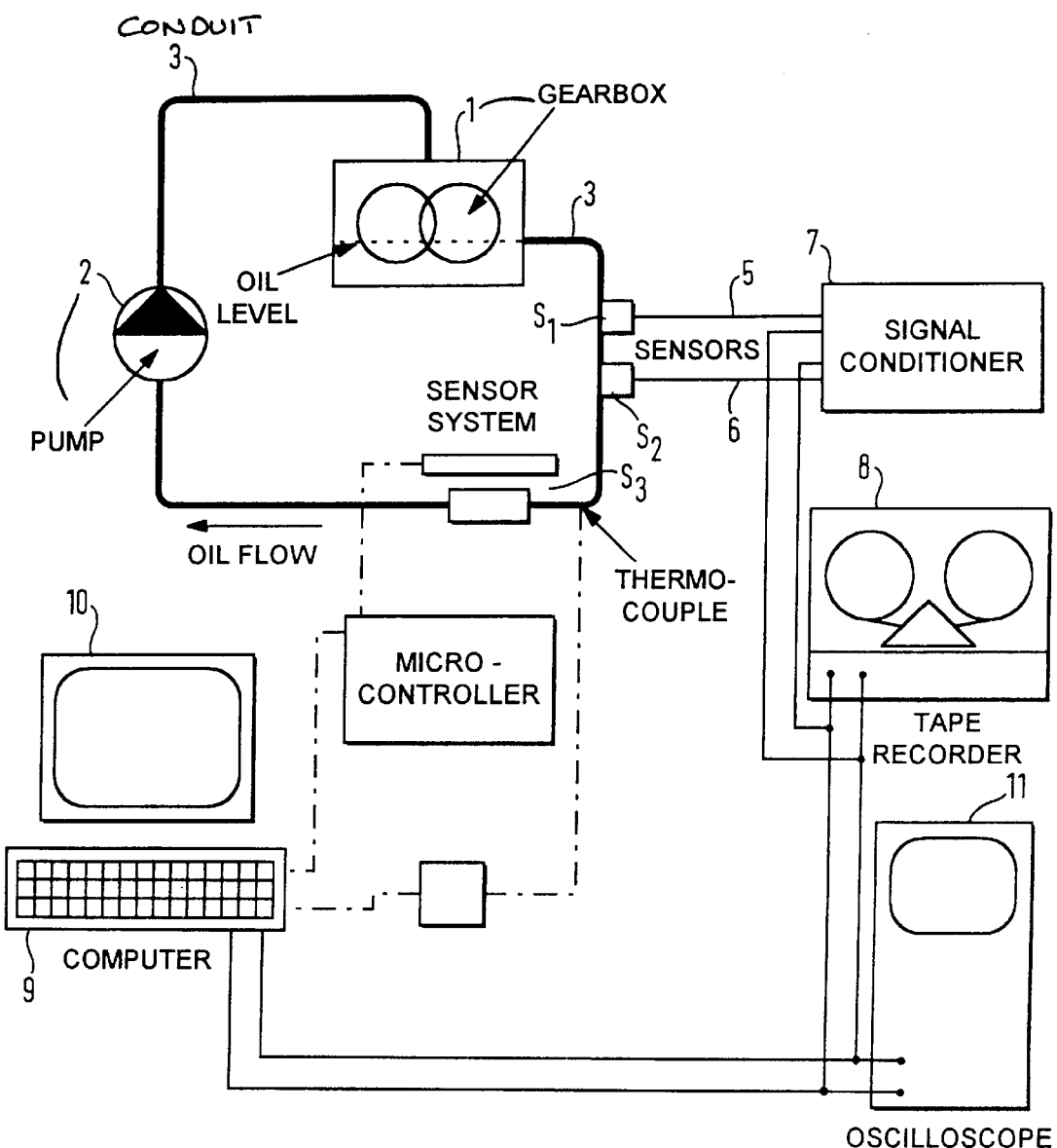
FIG. 1 is a schematic diagram of a lubrication monitoring system.

Conditioned signals from the signal conditioner 7 are recorded by a tape recorder 8 for subsequent analysis by a signal processing circuit, i.e. a computer 9. Alternatively, or additionally, the signal processing may be performed by the signal processing circuit 9 on-line and in real time. Results of the signal processing can be displayed on a display 10 in any suitable form for inspection by a user. An oscilloscope 11 may also be connected to the tape recorder 8 to allow a user to inspect the conditioned signals from the signal conditioner 7 prior to processing by the signal processing computer 9. Among other things the signal processing computer 9 processes the signals to determine the electrostatic activity level represented by the signals. The activity level is determined by calculating a rolling RMS value from the signals. Alternatively or additionally such methods as high and/or low pass filtering and/or Fast Fourier Transforms (FFTs) may be used by the signal processing computer to determine the electrostatic activity level in the lubricant as represented by the signals.

As oil flows through the conduit 3 electrostatic charge in the oil induces a signal onto each of the sensors S1, S2. Even with no debris present in the oil there will be a background signal induced by electrostatic charge generated in a similar manner and carried by the oil and from noise sources such as air bubbles and the like introduced by aeration of the oil. The signal conditioner 7 may include a high pass filter for filtering out low frequency noise from such noise sources detected by the sensors S1 and S2. The flow rate of the oil is known and it is also possible to use that knowledge to process the signals from the sensors to remove further noise therefrom.

The electrostatic charge and therefore the electrostatic signal vary with temperature of the lubricant. This temperature effect is compensated for by monitoring the lubricant temperature and the electrostatic signal when the lubricant is "clean", i.e. does not contain debris or other impurities. The temperature effect is repeatable, and the variation as temperature changes can therefore be predicted. The prediction is used as a baseline datum against which electrostatic and temperature signals are checked. The signal processing computer 9 is arranged to monitor for changes in the electrostatic signal which are different than those predicted in the baseline datum (i.e. different than those predicted and expected in advance against a given change in temperature).

Noise reduction techniques are used to increase the signal to noise ratio of the signals from the sensors. Further noise cancelling and signal processing techniques are described in WO 92/09886, the teachings of which are incorporated herein by reference.

The system shown in FIG. 1 further comprises a third sensor S3 with an associated microcontroller 12 for detecting debris in the oil in the conduit. The third sensor S3 is not necessary to put the invention into effect, it is merely included to provide a reference against which principles behind the invention will be explained. In tests a commercially available debris monitoring system was used to sense ferrous debris in the oil and it is the results of those tests that are shown in FIG. 2 of the accompanying drawings. The sensor S3 is temperature sensitive and the system therefore comprises a thermocouple to enable temperature corrections to be made. The commercially available system will not be described in any further detail herein.

In tests, an FZG lubricant testing machine was used as the gearbox 1. The FZG lubricant testing machine comprises gears which are configurable enable wear particles to be generated under known conditions, for example scuffing of the gears.

FIG. 2 of the drawings shows conditioned signals from the sensors S1 to S3 and a temperature signal from the thermocouple 14 obtained during a test run. As can be seen from FIG. 2, the test run lasted for some 3000 seconds (50 minutes) during which time conditions within the gearbox were varied. The conditioned signals from the electrostatic sensors S1 and S2 are represented by the dotted line 20, one conditioned output signal from the commercially available system sensor is represented by the line 21 and the temperature signal from the thermocouple is represented by the line 22.

The test gearbox was run under approximately steady conditions for about 1400 seconds to allow the gearbox to reach normal running temperatures. The test gearbox includes a cooling system (not shown) and after about 1400 seconds that was turned off. Then at about 1600 seconds a heater (not shown) was switched on to increase the operating temperature of the oil. At around 2200 seconds the speed of the gearbox was doubled and shortly thereafter a wear event occurred resulting in the generation of debris. The debris was detected by system sensor S3 as can be seen by the spike 23 in the line 21. The debris was also detected by the electrostatic sensors S1 and S2 as can be seen by the peak 24 in the line 20. The peak 24 is an electrostatic event and occurs before the spike 23 because, among other reasons, the sensors S1 and S2 are upstream of the sensor S3.

In the period between the heater being switched on and the engine speed being doubled (at which time the wear event occurred) there is a small but steady increase in the level of the signal 21 from the system sensor S3. It will be noted that this increase corresponds with the increase in temperature and is therefore a characteristic of the sensor rather than an indication of increased debris in the oil. A temperature-corrected signal from the system sensor would not exhibit such an increase. Until the wear event occurs at approximately 2300 seconds there is substantially no increase in debris in the oil.

In the same period there is a significant increase in the conditioned signal from the electrostatic sensors S1 and S2. These sensors are not temperature sensitive but the increase in signal level is greater than would be expected in advance from the pre-calculated baseline datum. The increase in signal level therefore corresponds to an increase in electrostatic activity within the oil. The increase in the sensed electrostatic activity is caused by an increase in physical/chemical reactions within the oil as a result of increased loadings of the oil in the gearbox.

Many lubricants, including the oil used during the test, contain an extreme pressure (EP) additive. The nature of EP additives is to adhere firmly to the surface of the metal of the gears in the gearbox. EP additives remain largely inactive until high contact temperatures are reached, typically 600–800° C. These are not bulk temperatures but occur when asperities interact. That is to say there will be local "hot-spots" on the gears and it is at those locations that the EP additives become active. At these high temperatures the EP additive molecule disassociates, producing chemically very active charged species which attack the high temperature metal creating an oxide type film which helps prevent contact welding (scuffing).

The electrostatic sensors detect the increase in charge species in the oil stream created by the EP chemical action; particles of the oxide film and byproducts of the dissociation are relatively highly charged because the oxide films are insulators and rubbing them together will cause electrostatic charge to be generated.

When the contact becomes more extreme with the doubling of the speed, the EP additive on the surface of the gear is overwhelmed and its contribution to the charge in the oil diminishes. Any metal-metal contact would then lead to contact welding, hence scuffing which generates particles, i.e. wear events, that are detected as electrostatic events by the electrostatic sensors and as signal spikes by the sensor in the usual manner.

The initial full metal-metal contact also provides an earthing route, quenching the charge level. This is another reason why the activity level of the electrostatic sensor signal falls just as the signal starts to indicate the presence of wear particles. However, it should be noted that the electrostatic sensor signal remains higher than earlier in the test. Also the signal is increased in amplitude compared to what would be predicted from a baseline datum at the appropriate oil temperature.

Should the wear become severe, then the bulk metal temperatures, i.e. the temperature of the gears in the gearbox, will rise rapidly, oxidising the oil and metal surface and creating charge-carrying carbon particles which are detectable by the electrostatic sensors. In a preliminary step-loaded scuffing test, where mild scuffing was not encountered, the heavy scuffing and over-heating was accompanied by high charge in the oil.

It will be appreciated from the foregoing that the use of an electrostatic sensor enables an increase in electrostatic activity resulting from increased loading or other adverse conditions to be detected. Such an increase in electrostatic activity is a precursor to a wear event and occurs as a result of physical/chemical reactions between the lubricant and the machine.

In the above discussed example there is a significant increase in the sensor signal before the wear event occurs. In some situations the precursor may not be represented by such a large change. The signal processing computer 9 may be arranged to increase the signal to noise ratio and emphasise the presence of the precursor by way of the above mentioned rolling RMS value, high and low pass filtering and FFT signal processing techniques for example. The operation of many machines is cyclic and advantage can be taken of this by the signal processing computer 9 in the use of said rolling RMS values, high and low pass filterings and FFTs to identify an event precursor in a signal.

Monitoring the electrostatic signal for a wear event precursor enables action to be taken before the event to avoid wear of the machine. Such avoiding action may simply be a reduction in operating speed/loading of the machine, or might involve an oil change either while the machine is running (if possible) or with the engine switched off. It can be seen from FIG. 2 that the precursor is detectable several minutes before the wear event. Even in an aircraft where engine shut-down was necessary this would give the pilot sufficient time to land safely without damaging the engine.

Having thus described the present invention by reference to a preferred embodiment it is to be well understood that the embodiment in question is exemplary only and that modifications and variations such as will occur to those possessed of appropriate knowledge and skills may be made without departure from the spirit and scope of the invention and equivalents thereof.

We claim:

1. An apparatus for detecting an impending wear event in a machine before its actual onset by monitoring a lubricant in a machine, the apparatus comprising a sensor for producing a signal representing electrostatic activity in a machine lubricant, and a signal processor for processing the signal from the sensor to detect an electrostatic activity precursor indicative of an impending wear event in the machine.

2. An apparatus as claimed in claim 1, wherein the signal processor is arranged to process the signal from the sensor to detect a change in the signal as representing the electrostatic activity precursor.

3. An apparatus as claimed in claim 1, wherein the signal processor is arranged to process the signal from the sensor to detect a steady increase in the amplitude of the signal as representing the electrostatic activity precursor.

4. An apparatus as claimed in claim 1, further comprising a signal conditioning circuit for conditioning signals from the sensor.

5. An apparatus as claimed in claim 4, wherein the signal conditioning circuit is connected to output conditioned signals to the signal processor.

6. An apparatus as claimed in claim 4, further comprising a recorder for recording signals from the sensor and/or from the signal conditioning circuit.

7. An apparatus as claimed in claim 6, further comprising an oscilloscope for displaying signals from the sensor, the signal conditioning circuit and/or the recorder.

8. An apparatus as claimed in claim 1, wherein the signal processor is operable in response to the detection of an electrostatic activity precursor to activate an indicator.

9. An apparatus as claimed in claim 1, wherein the sensor comprises a first electrostatic sensor for sensing electrostatics in lubricant at a first position in a machine and a second electrostatic sensor for sensing electrostatics at a second position in the said machine.

10. An apparatus as claimed in claim 1, wherein the sensor further comprises a temperature sensor, and the signal processor is operable in response to the temperature sensor for processing the signal representing electrostatic activity to compensate for temperature related changes thereto.

11. A method of detecting an impending wear event in a machine before its actual onset by monitoring a lubricant in a machine, the method comprising producing a signal representing electrostatic activity in a machine lubricant, and processing the signal to detect an electrostatic activity precursor indicative of an impending wear event in the machine.

12. A method as claimed in claim 11, wherein the signal is processed to detect a change therein as representing the electrostatic activity precursor.

13. A method as claimed in claim 11, wherein the signal is processed to detect a steady increase in the amplitude thereof as representing the electrostatic activity precursor.

14. A method as claimed in claim 11, further comprising conditioning the signal prior to said processing.

15. A method as claimed in claim 14, further comprising recording the signal and/or the conditioned signal.

16. A method as claimed in claim 15, further comprising displaying the signal, the conditioned signal, the recorded signal and/or the recorded conditioned signal.

17. A method as claimed in claim 11, further comprising sensing electrostatics in lubricant at a first position in a machine and sensing electrostatics in the lubricant at a second position in the said machine.

18. A method as claimed in claim 11, further comprising processing the signal representing electrostatic activity to compensate for temperature related changes thereto.

19. A method of detecting an impending wear event in a machine before its actual onset by monitoring a machine lubricating fluid, in which method the activity level of an electrostatic signal is monitored for a change which is interpreted as a precursor to an electrostatic event corresponding to an impending wear event.

20. A system for detecting an impending wear event in a machine before its actual onset by monitoring a machine lubricating fluid, in which system the activity level of an electrostatic signal is monitored for a change which is interpreted as a precursor to an electrostatic event corresponding to an impending wear event.

* * * * *